United States Patent [19]

Moore

[11] Patent Number: 4,973,545

[45] Date of Patent: Nov. 27, 1990

[54] PHOTOGRAPHIC COUPLERS WITH ARYLOXYSILYL GROUPS

[75] Inventor: Christopher P. Moore, Harrow, United Kingdom

[73] Assignee: Eastman Kodak Company, Rochester, N.Y.

[21] Appl. No.: 407,190

[22] Filed: Sep. 14, 1989

[30] Foreign Application Priority Data

Oct. 13, 1988 [GB] United Kingdom ................. 8824060

[51] Int. Cl.$^5$ .......................... G03C 7/38; G03C 7/32; G03C 7/34; G03C 7/36
[52] U.S. Cl. .................................... 430/376; 430/384; 430/385; 430/386; 430/387; 430/388; 430/389; 430/543; 430/546; 430/552; 430/553; 430/554; 430/556; 430/557; 430/558
[58] Field of Search ................ 430/543, 546, 552–558, 430/376, 384–389

[56] References Cited

U.S. PATENT DOCUMENTS 4,443,536  4/1984  Lestina ................................ 430/552

FOREIGN PATENT DOCUMENTS 0119860  9/1984  European Pat. Off. .
57-096338  6/1982  Japan .

OTHER PUBLICATIONS

*Research Disclosure*, Dec. 1978, Item #17643 Kenneth Mason Publications Ltd., Hampshire, England.

*Primary Examiner*—Richard L. Schilling
*Attorney, Agent, or Firm*—Richard E. Knapp

[57] ABSTRACT

A photographic coupler containing an aryloxysilyl group (—X—O—Y) wherein X is substituted or unsubstituted arylene and Y is a silyl group) is useful in photographic silver halide elements and processes. Such a photographic coupler enables improved dispersibility and improved photographic properties.

10 Claims, No Drawings

PHOTOGRAPHIC COUPLERS WITH ARYLOXYSILYL GROUPS

The invention relates to photographic couplers and to their use in photographic materials and processes.

Images are commonly obtained in the photographic art by a coupling reaction between the development product of a silver halide color developing agent (such as, oxidized aromatic primary amino developing agent) and a color forming compound commonly referred to as a coupler. The dyes produced by coupling are indoaniline, azomethine, indamine or indophenol dyes, depending upon the chemical composition of the coupler and the developing agent. The subtractive process of color formation is ordinarily employed in multicolor photographic elements and the resulting image dyes are usually cyan, magenta and yellow dyes. These dyes are formed in or adjacent to silver halide layers sensitive to radiation complementary to the radiation absorbed by the image dye such as silver halide emulsion layers sensitive to red, green and blue radiation, respectively.

The patent and technical literature is replete with references to compounds which can be used as couplers for the formation of photographic images. Preferred couplers which form cyan dyes upon reaction with oxidized color developing agents are phenols and naphthols. Representative couplers are described in the following patents and publications: U.S. Pat. Nos. 2,772,162, 2,895,826, 3,002,836, 3,034,892, 2,474,293, 2,423,730, 2,367,531, 3,041,236, 4,333,999 and "Farbkuppler-eine Literaturubersicht" published in Agfa Mitteilungen, Band III, pp. 156-175 (1961).

Couplers which form yellow dyes upon reaction with oxidized color developing agent are acylacetanilides such as benzoylacetanilides and pivalylacetanilides. Representative couplers are described in the following patents and publications: U.S. Pat. Nos. 2,875,057, 2,407,210, 3,265,506, 2,298,443, 3,048,194, 3,447,928 and "Farbkuppler-eine Literaturubersicht," published in Agfa Mitteilungen, Band III, pp, 112-126 (1961).

Preferred couplers which form magenta dyes upon reaction with oxidized color developing agent are pyrazolones, pyrazolotriazoles, pyrazolobenzimidazoles and indazolones. Representative couplers are described in such patents and publications as U.S. Pat Nos. 2,600,788, 2,369,489, 2,343,703, 2,311,082, 2,673,801, 3,152,896, 3,519,429, 3,061,432, 3,062,653, 3,725,067, 2,908,573 and "Farbkuppler-eine Literaturubersicht," published in Agfa Mitteilungen, Band III, pp. 126-156 (1961).

Japanese Published Patent Application No. 57-96338 describes a magenta dye-forming coupler in which the pyrazolone ring is substituted in the 4-position with a silyloxy group. Such couplers are said to provide improved optical density and low fog in the developed image.

EPA-A-0 073 636 describes photographic couplers having attached to a position other than the coupling position a ballast group terminated with a hydroxyphenylsulfonyl group or a hydroxyphenylsulfinyl group. The couplers are said to have improved stability, reactivity and compatibility with other components in a photographic element.

When intended for incorporation in photographic elements, couplers are commonly dispersed therein with the aid of a high boiling point organic solvent, referred to as a coupler solvent.

There is a continuing need to provide couplers having improved dispersibility. In pursuance of this need, it has now been discovered that the dispersibility of couplers containing a hydroxyaryl group, other than a hydroxyaryl group necessary to provide coupling activity, can be improved by silylating the hydroxy group. This modification can also result in improved photographic properties such as increased photographic speed, enhanced dye hue characteristics or enhanced dark stability of the derived image dye.

The invention provides a photographic element comprising a support bearing at least one photographic silver halide emulsion layer and a photographic coupler comprising a coupler moiety and an aryloxysilyl group. The photographic coupler is represented by the formula:

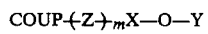

wherein COUP is a coupler moiety, such as a cyan, magenta or yellow dye-forming coupler moiety; Z is a linking group or atom, such as oxy (—O—), alkyleneoxy, arleneoxy, sulfonyl, alkylenesulfonyl or arylenesulfonyl; X is unsubstituted or substituted arylene, such as phenylene; Y is a silyl group; and m is 0 or 1.

The photographic element is preferably a color photographic silver halide element and the coupler is a non-diffusible dye-forming coupler.

The coupler of the invention can be derived from any known coupler and reacts with oxidized color developing agent to form a dye.

Preferred couplers have the structural formula

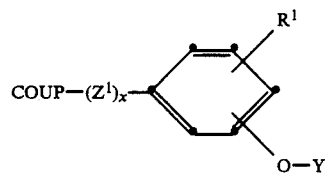

wherein

COUP represents a dye-forming coupling group, preferably having $Z^1$ bonded at the coupling position of COUP;

$Z^1$ is oxy, alkyleneoxy, aryleneoxy, sulfonyl, alkylenesulfonyl or arylenesulfonyl;

x is 0 or 1;

$R^1$ is hydrogen or one or more substituents, such as halogen, alkyl, alkoxy, aryl, aryloxy, acyl or sulfonyl; and, Y is a silyl group.

Preferred silyl groups are represented by the formula

wherein $R^2$, $R^3$ and $R^4$ are individually substituted or unsubstituted alkyl, cycloalkyl, or aryl groups.

Preferably, $R^2$, $R^3$ and $R^4$ are individually a substituted or unsubstituted alkyl group having from 1 to 16 carbon atoms, a substituted or unsubstituted cycloalkyl group having from 3 to 6 carbon atoms or a substituted or unsubstituted aryl group having from 6 to 18 carbon atoms. More preferably, at least one of the groups is a branched alkyl group, such as i-propyl or t-butyl, a substituted cycloalkyl group, such as methylcyclohexyl, or a substituted aryl group, such as t-butylphenyl. Suitable substituents for $R^2$, $R^3$ and $R^4$ include alkyl, aryl and sulfonyl groups and halogen atoms.

The coupling group represented by COUP may be any known dye-forming coupling group. The coupling position of the coupling may be unsubstituted or substituted with a coupling off group which can modify the equivalency of the coupler. The remainder of the coupler molecule shown attached to COUP may be joined to the coupling group at any position. The coupling group can be ballasted or unballasted. The coupler can be monomeric, or it can be a dimeric, oligomeric or a polymeric coupler.

Representative dye-forming coupling groups contain the structures shown below. In these structures K represents hydrogen or a coupling off group and the unsatisfied bond, or bonds, indicates the preferred position, or positions, at which there can be attached substituents forming part of COUP.

Examples of cyan dye-forming coupling groups include

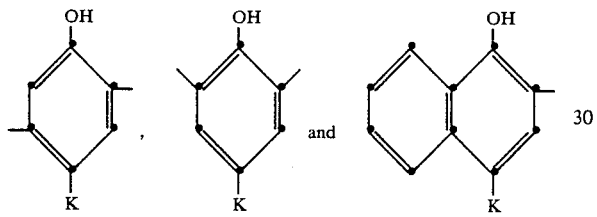

Examples of magenta dye-forming coupling groups include:

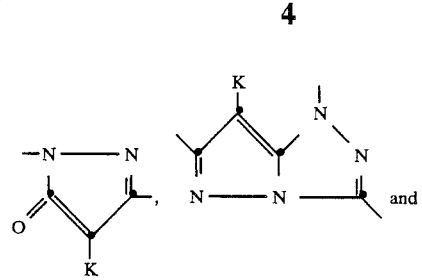

Examples of yellow dye-forming coupling group include:

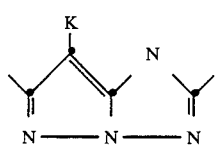

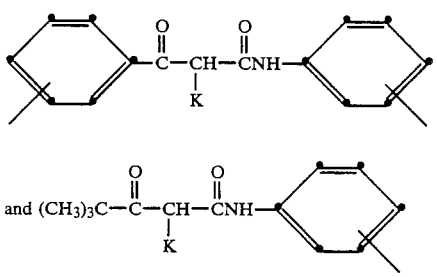

The —X—O—Y group defined above can be linked directly to a coupling group as shown in the above structural formulae or it can form part of a substituent in such a coupling group. A common substituent found in image dye-forming couplers is a ballast group. This group is located on the coupler in a position other than the coupling position and imparts to the coupler sufficient bulk to render the coupler non-diffusible in a photographic element as coated and during processing.

Specific examples of couplers of the invention are as follows:

Formula I:

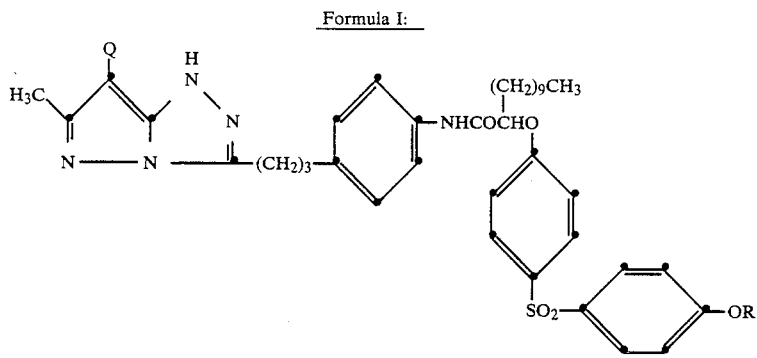

Coupler No. 1 Q = Cl
R = Si(CH$_3$)$_2$t-C$_4$H$_9$

Coupler No. 2 Q = H
R = Si(CH$_3$)$_2$t-C$_4$H$_9$

Formula II:

-continued

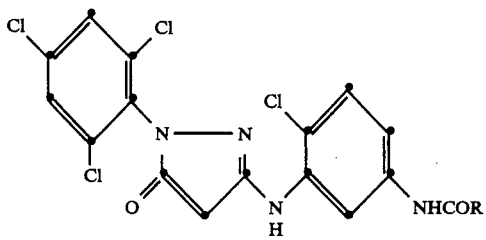

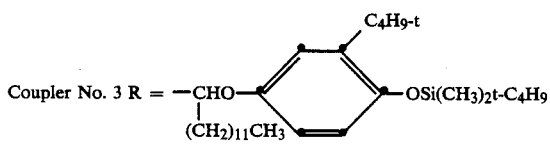

Coupler No. 3 R =

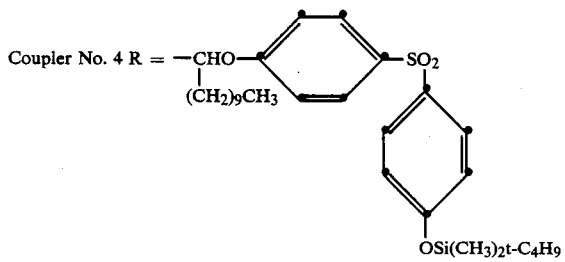

Coupler No. 4 R =

Formula III:

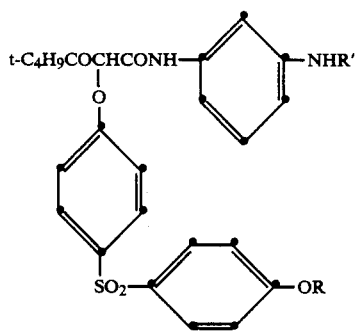

Coupler No. 5 R = Si(CH$_3$)$_2$t-C$_4$H$_9$
R' = SO$_2$(CH$_2$)$_{15}$CH$_3$

Coupler No. 6 R = Si(CH$_3$)$_2$t-C$_4$H$_9$

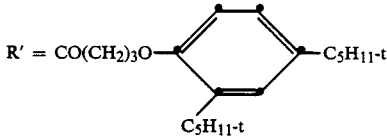

Methods of preparing photographic color couplers are well known and documented. The couplers of the invention may be prepared from couplers containing a hydroxyaryl group other than a hydroxyaryl group necessary to provide coupling activity. Many such couplers and methods of preparing them are described in the patent literature and some are available commercially, such as the coupler of Formula I above in which R=H. Silylation of the hydroxy-containing coupler by methods known in the art will produce a coupler of the invention.

As described in detail hereinafter in the specific examples of the preparation of couplers of the invention, the couplers may be made by reacting a halosilane, preferably a chlorosilane, with a coupler containing a hydroxyaryl group.

Preparation of Couplers Nos. 1-6

The following method was used to prepare each of the couplers.

The appropriate hydroxy containing coupler (30 mmol) was suspended in anhydrous acetonitrile (600 ml); anhydrous 1-hydroxybenzotriazole (13.3 mmol, 1.8 g) and t-butyldimethylchlorosilane (90 mmol, 13.59 g) were added with stirring and the mixture was cooled to 0° C. Triethylamine (225 mmol, 22.77 g) was added dropwise and the mixture was allowed to warm up to room temperature and then heated to a gentle reflux for 2-5 h monitoring by TLC (33% ethyl acetate/60-80 petrol). In some cases the reaction could be effected by maintaining the mixture at room temperature overnight. When cool the solvent was removed and the residue wa partitioned between ethyl acetate (300 ml) and water (300 ml). The aqueous phase was extracted with ethyl acetate (2×300 ml) and the combined organic phases were dried and evaporated under reduced pressure to leave the product as a viscous oil. Purification was achieved by chromatography (SiO$_2$: 20% ethyl acetate/60–80 petrol) and/or recrystallization. All NMR, IR, MS and analytical data were consitent with theproducts.

Characteristic IR: 900–910 (SiO).
Characteristic NMR: $\delta$ 0.25 (s, 6H, SiMe$_2$), 1.0 (s, 9H, Sit-Bu).

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated with" signifies that the coupler is incorporated in the silver halide emlusion layer or in a layer adjacent thereto where, during processing, it is capable of reacting with silver halide development products.

The photographic elements can be single color elements or multicolor elements. In a multicolor element, the yellow dye-forming couplers of this invention are typically associated with a blue-sensitive emulsion, although they can be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing photographic silver halide emulsion layer units sensitive to the red-, green-, or blue- regions of the spectrum and containing, respectively, at least one cyan-, magenta-, or yellow dye-forming coupler, the coupler of the invention being in at least one of the emulsion layer units. The element can contain additional layers, such as filter layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein.

The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section X), coating aids (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethaylaniline hydrochloride, 4-amino-3-methyl-N-ethyl-N-$\beta$-(methanesulfonamido)ethylaniline sulphate hydrate, 4-amino-3-methyl-N-ethyl-N-$\beta$-hydroxyethylaniline sulphate, 4-amino3-$\beta$-(methanesulfonamido)ethyl-N,N-diethylaniline hydrochloride and 4-amino-N-ethyl-N-ethyl-N-(2-methoxyethyl)-m-toluidine di-p-toluene sulfonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples further illustrate the invention.

Photographic Testing

The methods of photographic testing used in the Examples below are carried out as follows.

(i) Preparation of Experimental Photographic Coatings

Each coupler of the invention and each comparison coupler was dissolved in half its weight of tricresylphosphate as the coupler solvent using 2-(2-butoxyethoxy)ethyl acetate as the auxiliary solvent. The coupler was dispersed in a gelatin solution and the auxiliary solvent was removed by evaporation under reduced pressure.

Experimental photographic coatings were prepared by coating a cellulose acetate film support with a photosensitive layer comprising a dispersion of the coupler as formulated above coated at a laydown of 1.04 mmol m$^{-2}$, a silver chlorobromide emulsion at 1.61 gm$^{-2}$ Ag, gelatin at 2.42 gm$^{-2}$ and a hardener at 0.06 gm$^{-2}$. An overcoat containing gelatin at 1.5 gm$^{-2}$ was applied to the photosensitive layer.

The dried experimental coating was then slit and chopped into test strips.

(ii) Sensitometric Testing

The test strips were exposed through a neutral density step-wedge test object. The strips were then processed through a standard C41 processing cycle as described in the British Journal of Photographic Annual 1977, pages 204–5. The processed strips were then dried to give stepped dye images.

For each test strip step wedge densities were measured by transmission densitometry and sensitometric curves were constructed. Measurements were made of photographic speed.

(iii) Spectrophotometric Testing

Test strips were exposed as above through a step-wedge test object and appropriate filters to give to give an optical density of about 1.0. The strips were processed using the standard conditions described above and samples cut from the dye image step with density closest to 1.0. Visible absorption spectra (normalized to 1.0 density) were obtained using a spectrophotometer.

Dye hues are expressed in terms of the wavelength corresponding to the maximum absorption peak ($\lambda$max) and the half-bandwidth (HBW) calculated from the spectrophotometric curves.

(iv) Dye Stability Testing

Dye sample patches having a density of about 1.0 were prepared as for spectrophotometric testing and their absorption spectram measured as above.

For the dark keeping experiment, the dye samples were incubated in a dark oven for periods of 1,3 and 6 weeks at a constant 60° C. and 70% relative humidity. The spectrophotometric curves of the samples were then remeasured and the degree of fade quoted as the fractional decrease in density at the absorption maximum relative to the initial density prior to fading. The results are presented as dark/wet fade data.

(v) Dye Dispersibility

An experiment to demonstrate the dispersiblity of a coupler was conducted by measuring the solubility of the coupler in di-n-butylphthalate as the coupler solvent using a steam bath at 80° C.

In the following Examples, Couplers 1 to 6 are as defined above. Comparison Couplers C-1 to C-6 have the same structures as Couplers 1 to 6, respectively, except that the silyl group is replaced by a hydrogen atom. For example, Coupler C-1 has the structure depicted by Formula I wherein Q=Cl and R=H.

EXAMPLE 1

Solubility data for Couplers 1 and C-1 are as follows.

| Coupler | Weight (mg) | Solvent (ml) | Time on Steam Bath (min) | Solubility |
|---|---|---|---|---|
| C-1 | 100 | 1 | 6 | insoluble |
| C-1 | 80 | 1 | 6 | partially soluble |
| C-1 | 60 | 1 | 6 | soluble with agitation |
| C-1 | 40 | 1 | 6 | soluble |
| C-1 | 20 | 1 | 2 | soluble |
| 1 | 80 | 0.1 | 1 | soluble |
| 1 | 80 | 0.05 | 1 | soluble |

It is clear from the results that Coupler No. 1 is greater than ten times more soluble than Coupler C-1 under these conditions.

Couplers 2 to 6 also show greatly improved solubility in organic solvents when compared to Couplers C-2 to C-6, respectively.

EXAMPLE 2

The dark/wet fade data for Couplers 1, 3 and 5 and for Couplers C-1, C-3 and C-5 are as follows.

| Coupler | Dark/Wet Fade | | |
|---|---|---|---|
| | 1 wk | 2 wk | 3 wk |
| 1 | +0.02 | +0.01 | 0.00 |
| C-1 | +0.07 | +0.05 | +0.06 |
| 3 | −0.02 | −0.04 | −0.09 |
| C-3 | −0.04 | −0.08 | −0.09 |
| 5 | +0.03 | −0.02 | −0.16 |
| C-5 | +0.06 | +0.07 | +0.04 |

The results show that couplers of the invention are capable of providing improved dark stability.

EXAMPLE 3

Photographic speed and dye hue data for Couplers 1, 3, 4 and 5 and for Couplers C-1, C-3, C-4 and C-5 are as follows.

| Coupler | Speed | $\lambda$max | HBW |
|---|---|---|---|
| 1 | 321 | 548.5 | 86.5 |
| C-1 | 298 | 553 | 89.5 |
| 3 | 311 | 539.5 | 78.5 |
| C-3 | 316 | 544.5 | 82 |
| 4 | 317 | 541.5 | 84.5 |
| C-4 | 317 | 545.5 | 92 |
| 5 | 378 | 448 | 90 |
| C-5 | 372 | 449 | 95.5 |

The results show some of the couplers of the invention having improved photographic speed while all the couplers are characterized as having slightly hypsochromic but sharper dye absorptions.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and a photographic coupler comprising a coupler moiety containing an aryloxysilyl group.

2. A photographic element as in claim 1 wherein the photographic coupler is represented by the formula:

COUP―(Z)ₘ―X―O―Y wherein COUP is a coupler moiety; Z is a linking group or atom; X is unsubstituted or substituted arylene; Y is a silyl group; and m is 0 or 1.

3. A photographic element as in claim 1 wherein the photographic coupler is represented by the formula:

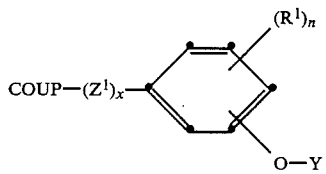

wherein COUP is a dye-forming coupler group; $Z^1$ is oxy, alkyleneoxy, aryleneoxy, sulfonyl, alkylenesulfonyl or arylenesulfonyl; x is 0 or 1; $R^1$ is halogen, alkyl, alkoxy, aryl, aryloxy, acyl or sulfonyl; n is 0, 1, 2 or 3; and, Y is a silyl group.

4. A photographic element as in claim 1 wherein the silyl group is represented by the formula:

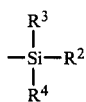

wherein $R^2$, $R^3$ and $R^4$ are each individually substituted or unsubstituted alkyl, cycloalkyl or aryl groups.

5. A photographic element as in claim 4 wherein $R^2$, $R^3$ and $R^4$ are each individually substituted or unsubstituted alkyl containing 1 to 16 carbon atoms, a substituted or unsubstituted cycloalkyl group containing 3 to 6 carbon atoms or a substituted or unsubstituted aryl group containing 6 to 18 carbon atoms.

6. A photographic element as in claim 4 wherein at least one of $R^2$, $R^3$ and $R^4$ is a branched alkyl group, a substituted cycloalkyl group, or a substituted aryl group.

7. A photographic element as in claim 1 wherein the coupler is at least one of:

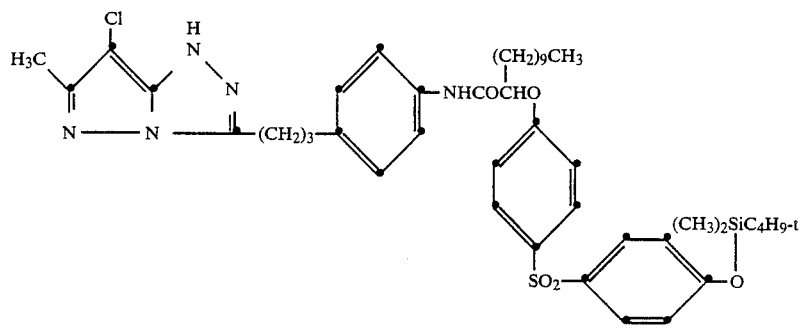

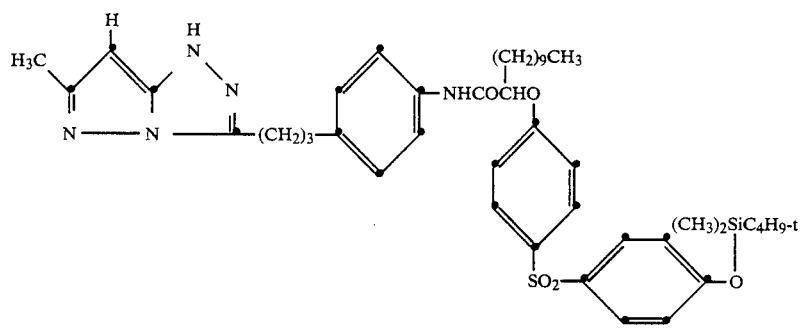

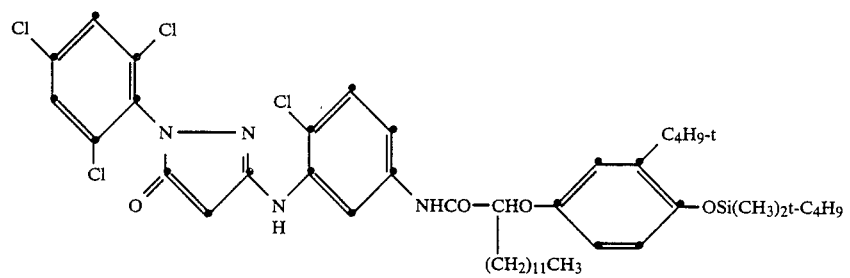

-continued

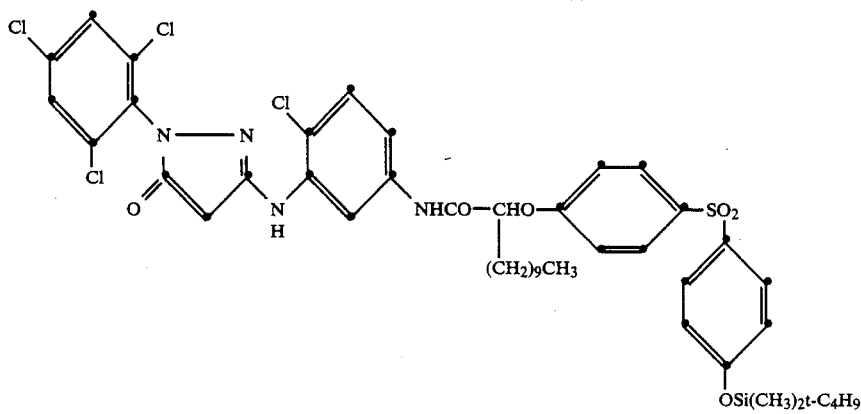

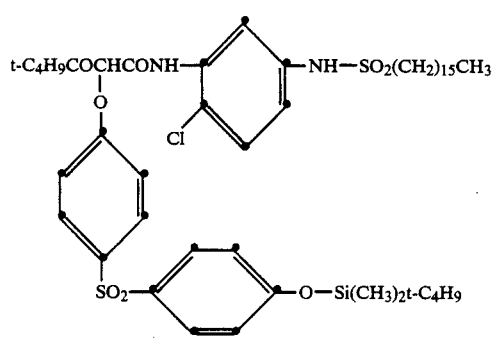

and

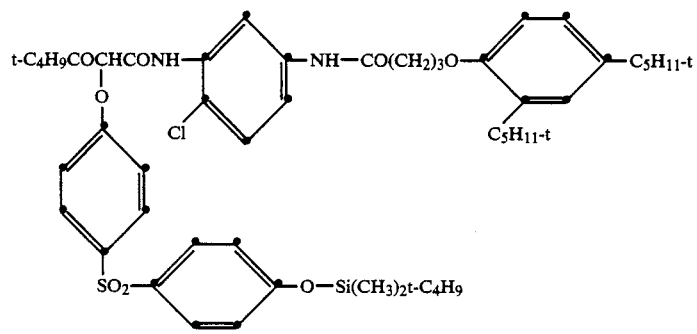

8. A photographic element as in claim 1 comprising a multilayer, multicolor photographic element comprising photographic silver halide emulsion layer units sensitive to the red-, green-, or blue- regions of the spectrum and containing, respectively, at least one cyan-, magenta-, or yellow dye-forming coupler, the coupler containing the silyl group as defined in claim 1 being in at least one of the emulsion layer units.

9. A process of forming a photographic image that comprises developing an exposed photographic silver halide emulsion layer with a color developing agent in the presence of a coupler as defined in claim 1.

10. A process as in claim 9 wherein the couplers is as defined in claim 2.

* * * * *

UNITED STATES PATENT AND TRADEMARK OFFICE
CERTIFICATE OF CORRECTION

PATENT NO. : 4,973,545
DATED : November 27, 1990
INVENTOR(S) : Christopher P. Moore It is certified that error appears in the above-identified patent and that said Letters Patent is hereby corrected as shown below:

Title page, first column, item [30], line 2, "8824060" should read --8824060.1--. Column 2, line 23, "arleneoxy" should read --aryleneoxy--. Column 3, line 9, "coupling may" should read --coupling group may--. Column 4, line 18, "group" should read --groups--. Column 5, formula III, that part of formula reading

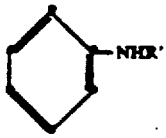     should read     

Column 7, line 11, "consitent" should read --consistent--. Column 8, line 35, that part of formula reading "diethaylaniline" should read --diethylaniline--. Column 9, line 42, "spectram" should read --spectra--; line 54, "dispersiblity" should read --dispersibility--.

Signed and Sealed this

Twenty-first Day of April, 1992

Attest:

HARRY F. MANBECK, JR.

*Attesting Officer*        *Commissioner of Patents and Trademarks*